US012643092B2

(12) United States Patent
Chien et al.

(10) Patent No.: US 12,643,092 B2
(45) Date of Patent: Jun. 2, 2026

(54) DEODORIZATION FIBER AND MANUFACTURE METHOD THEREOF

(71) Applicant: TAIWAN TEXTILE RESEARCH INSTITUTE, New Taipei City (TW)

(72) Inventors: Chih-Min Chien, New Taipei City (TW); Rih-Sheng Chiang, New Taipei City (TW)

(73) Assignee: TAIWAN TEXTILE RESEARCH INSTITUTE, New Taipei City (TW)

( * ) Notice: Subject to any disclaimer, the term of this patent is extended or adjusted under 35 U.S.C. 154(b) by 498 days.

(21) Appl. No.: 18/452,605

(22) Filed: Aug. 21, 2023

(65) Prior Publication Data

US 2024/0100511 A1     Mar. 28, 2024

(30) Foreign Application Priority Data

Sep. 22, 2022     (TW) .................................. 111135975

(51) Int. Cl.
| | |
|---|---|
| *B01J 27/16* | (2006.01) |
| *A61L 9/014* | (2006.01) |
| *B01J 31/02* | (2006.01) |
| *B01J 31/06* | (2006.01) |
| *B01J 31/38* | (2006.01) |
| *B01J 35/58* | (2024.01) |
| *B01J 37/00* | (2006.01) |
| *B01J 37/04* | (2006.01) |

(52) U.S. Cl.
CPC .............. *B01J 27/16* (2013.01); *A61L 9/014* (2013.01); *B01J 31/0237* (2013.01); *B01J 31/06* (2013.01); *B01J 31/38* (2013.01); *B01J 35/58* (2024.01); *B01J 37/0036* (2013.01); *B01J 37/04* (2013.01); *A61L 2209/22* (2013.01)

(58) Field of Classification Search
CPC ...... A61L 9/014; A61L 2209/22; B01J 27/16; B01J 31/0237; B01J 31/06; B01J 31/38; B01J 35/58; B01J 37/0036; B01J 37/04; D01F 1/10; D01F 1/103; D01F 6/62
See application file for complete search history.

(56) References Cited

U.S. PATENT DOCUMENTS 8,236,291 B2     8/2012     Sakamoto
2003/0118664 A1*     6/2003     Trogolo .................. C08K 9/08
424/641

FOREIGN PATENT DOCUMENTS

TW          I410548  B     10/2013

* cited by examiner

*Primary Examiner* — Brian A Mccaig
(74) *Attorney, Agent, or Firm* — McClure, Qualey & Rodack, LLP

(57) ABSTRACT

A manufacture method of a deodorization fiber includes: a mixing step including mixing zirconium phosphate and a first dispersant including an amine-group compound in a solvent to form a mixture; a grinding step including grinding the mixture until a D90 particle size of zirconium phosphate is 0.1 μm to 1.5 μm to form a grinded mixture; a heating and stirring step including heating and stirring the grinded mixture to uniformly distribute zirconium phosphate and the first dispersant in the solvent to form a deodorant; a blending and pelletizing step including blending and pelletizing the deodorant and polyester to form a fiber masterbatch; and a melt spinning step including melt spinning the fiber masterbatch to form the deodorization fiber. A deodorization fiber is further provided.

10 Claims, 2 Drawing Sheets

100

100

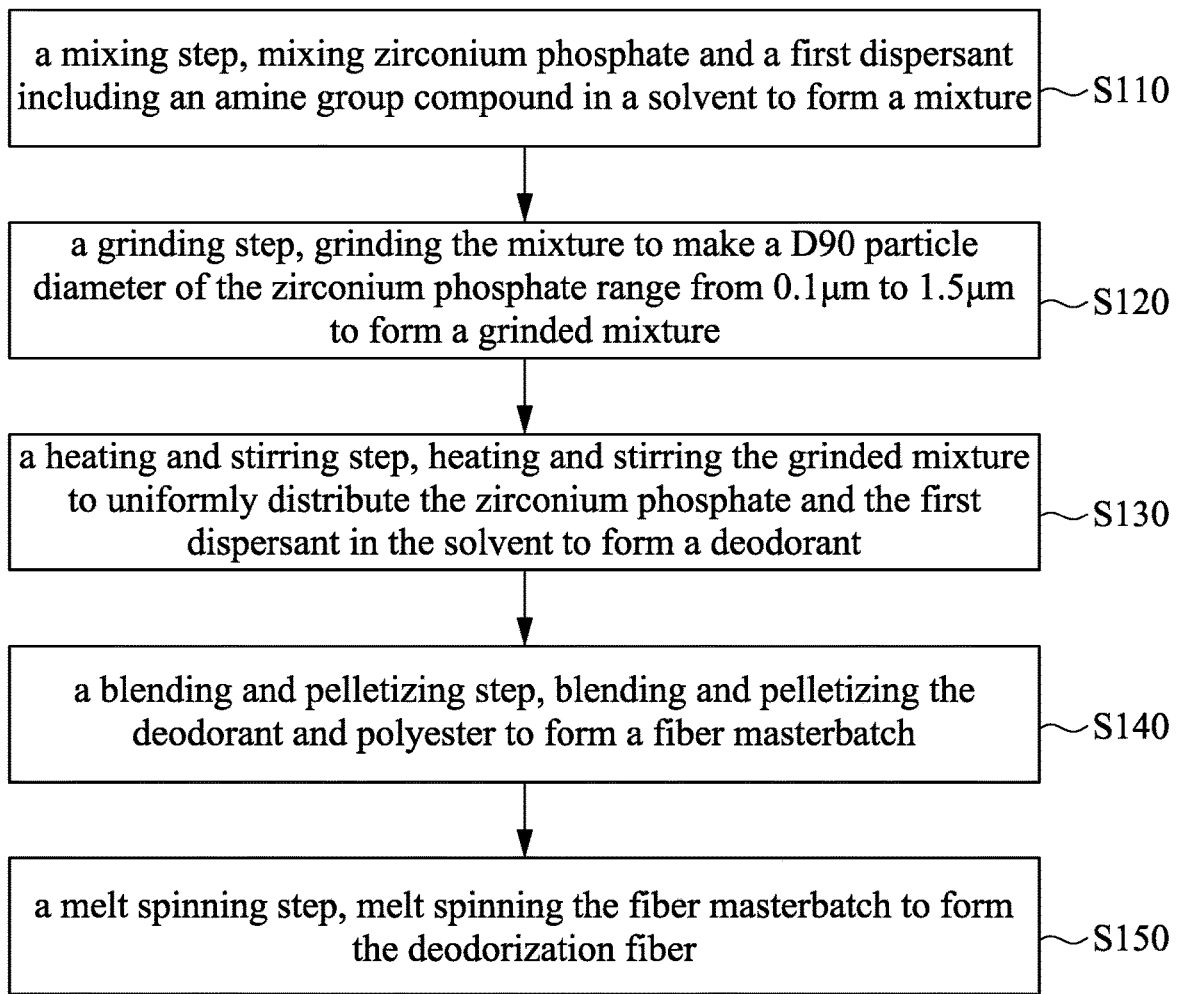

a mixing step, mixing zirconium phosphate and a first dispersant including an amine group compound in a solvent to form a mixture — S110 a grinding step, grinding the mixture to make a D90 particle diameter of the zirconium phosphate range from 0.1μm to 1.5μm to form a grinded mixture — S120 a heating and stirring step, heating and stirring the grinded mixture to uniformly distribute the zirconium phosphate and the first dispersant in the solvent to form a deodorant — S130 a blending and pelletizing step, blending and pelletizing the deodorant and polyester to form a fiber masterbatch — S140 a melt spinning step, melt spinning the fiber masterbatch to form the deodorization fiber — S150

Fig. 1

DEODORIZATION FIBER AND MANUFACTURE METHOD THEREOF

CROSS-REFERENCE TO RELATED APPLICATION

This application claims priority to Taiwan Application Serial Number 111135975, filed Sep. 22, 2022, which is herein incorporated by reference.

BACKGROUND

Field of Invention

The present disclosure relates to a deodorization fiber and a manufacture method thereof. In particular, the present disclosure is related to a deodorization fiber includes zirconium phosphate and an amine group compound.

Description of Related Art

Fiber is widely used on various fabrics because of its good elasticity, stretchability and quick-drying property, in which a deodorization fiber has great potential for sportswear applications since the deodorization fiber can remove odor. However, a deodorization rate of the known deodorization fiber is less than 50%, and the deodorization effect is limited.

Therefore, how to provide a deodorization fiber with enhanced deodorization effect is a problem to be solved.

SUMMARY

The present disclosure provides a deodorization fiber and a manufacture method of the deodorization fiber, in which the deodorization effect of the deodorization fiber is enhanced by realizing double deodorization of the deodorization fiber.

According to an embodiment of the present disclosure, the manufacture method of the deodorization fiber includes: a mixing step, mixing zirconium phosphate and a first dispersant including an amine group compound in a solvent to form a mixture; a grinding step, grinding the mixture to make a D90 particle diameter of the zirconium phosphate range from 0.1 μm to 1.5 μm to form a grinded mixture; a heating and stirring step, heating and stirring the grinded mixture to uniformly distribute the zirconium phosphate and the first dispersant in the solvent to form a deodorant; a blending and pelletizing step, blending and pelletizing the deodorant and polyester to form a fiber masterbatch; and a melt spinning step, melt spinning the fiber masterbatch to form the deodorization fiber.

In one embodiment of the present disclosure, the mixing step includes mixing 25 parts by weight to 40 parts by weight of the zirconium phosphate and 5 parts by weight to 15 parts by weight of the first dispersant in 55 parts by weight to 65 parts by weight of the solvent.

In one embodiment of the present disclosure, the first dispersant further includes fatty alcohol ether, organic acid ester, or a combination thereof.

In one embodiment of the present disclosure, an amount of the amine group compound is from 5 parts by weight to 15 parts by weight based on an amount of the first dispersant as 100 parts by weight.

In one embodiment of the present disclosure, at the blending and pelletizing step, the polyester is from 80 parts by weight to 95 parts by weight, and the zirconium phosphate is from 5 parts by weight to 20 parts by weight.

In one embodiment of the present disclosure, the manufacture method of the deodorization fiber further includes adding a second dispersant, in which the second dispersant includes a polyester dispersant, a paraffin dispersant, or a combination thereof at the blending and pelletizing step.

In one embodiment of the present disclosure, at the blending and pelletizing step, the polyester is from 80 parts by weight to 95 parts by weight, the zirconium phosphate is from 5 parts by weight to 20 parts by weight, and the second dispersant is from 1 part by weight to 5 parts by weight.

In one embodiment of the present disclosure, a temperature of the blending and pelletizing step is from 250° C. to 300° C.

According to an embodiment of the present disclosure, a deodorization fiber includes polyester, zirconium phosphate and an amine group compound. A D90 particle diameter of the zirconium phosphate is from 0.1 μm to 1.5 μm.

In one embodiment of the present disclosure, a weight ratio of the zirconium phosphate and the amine group compound is from 10:1 to 100:1.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 1 depicts a flowchart of a manufacture method of a deodorization fiber.

DETAILED DESCRIPTION

Figure 2:
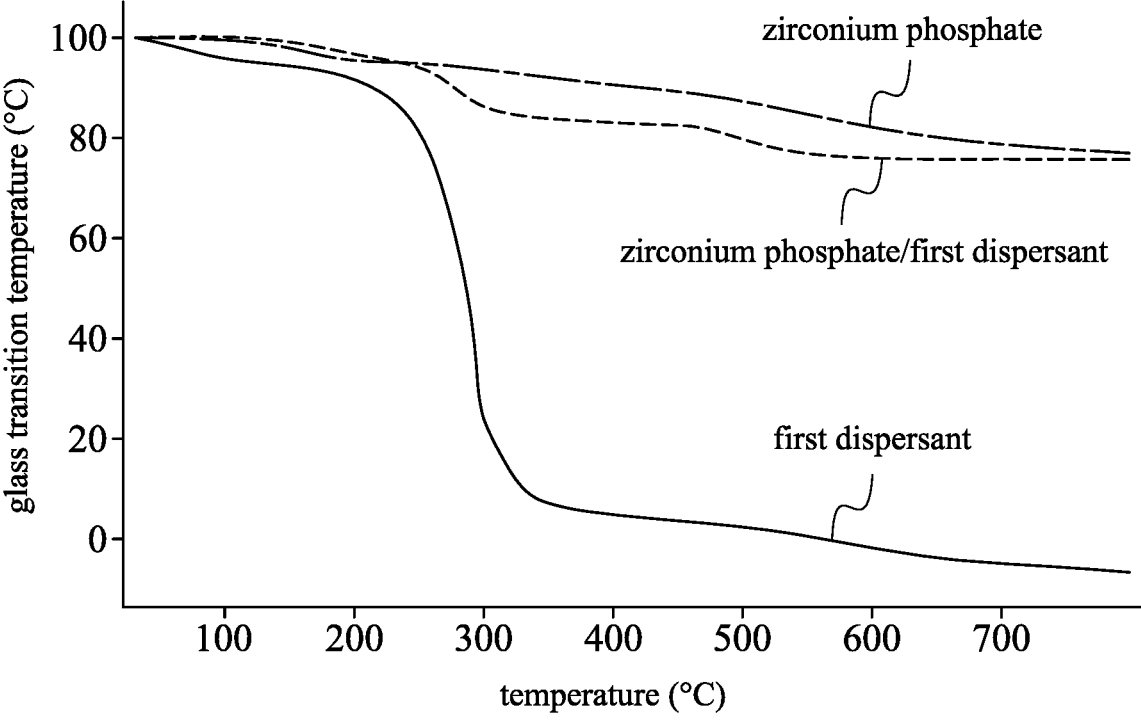
FIG. 2 illustrates a change chart of a glass transition temperature for each condition under the three conditions of zirconium phosphate, a first dispersant, and a combination of zirconium phosphate and the first dispersant as the temperature increased.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The device may be otherwise oriented (rotated 90 degrees or at other orientations) and the spatially relative descriptors used herein may likewise be interpreted accordingly.

The present disclosure provides a deodorization fiber and manufacture method thereof, in which the deodorization fiber includes zirconium phosphate and an amine group compound, exhibiting excellent deodorization effect for ammonia and acetic acid, respectively. The dispersibility can be enhanced by regulating a D90 particle diameter of zirconium phosphate be ranging from 0.1 μm to 1.5 μm, and the deodorization effect of ammonia can be further enhanced. In addition, the heat resistance of the amine group compound is enhanced in the process for manufacturing the deodorization fiber by the charge attraction of positive charge and negative charge of zirconium phosphate and the amine group compound, and the dispersibility of zirconium phosphate can be enhanced by the amine group compound. The double deodorization (for example, a deodorization rate of ammonia gas is 84%, and a deodorization rate of acetic acid is 79%) is realized by the abovementioned synergistic effect of zirconium phosphate and the amine group compound, thereby increasing the deodorization effect of the deodorization fiber.

Please refer to FIG. 1, one embodiment of the present disclosure depicts a flowchart of a manufacture method 100 of a deodorization fiber, in which the manufacture method 100 includes from step S110 to step S150.

Step S110 is a mixing step, mixing zirconium phosphate and a first dispersant including an amine group compound in a solvent to form a mixture.

In some embodiments, the solvent is water. In some embodiments, the amine group compound includes primary amine, secondary amine, or a combination thereof.

In some embodiments, the mixing step includes mixing 25 parts by weight to 40 parts by weight of zirconium phosphate and 5 parts by weight to 15 parts by weight of the first dispersant in 55 parts by weight to 65 parts by weight of the solvent. The first dispersant is used to increase the dispersibility of zirconium phosphate to increase the following grinding effect. Therefore, if a weight ratio of zirconium phosphate to the first dispersant is too high, the subsequent grinding effect will be poor. Conversely, if the weight ratio is too low, multiple treatments are required to obtain the desired amount of zirconium phosphate, and the time required for the process is prolonged.

In some embodiments, an amount of the amine group compound is from 5 parts by weight to 15 parts by weight based on an amount of the first dispersant as 100 parts by weight. In some embodiments, the first dispersant further includes fatty alcohol ether, organic acid ester, or a combination thereof. For example, the amount of the amine group compound in the first dispersant is from 5 parts by weight to 15 parts by weight, the amount of fatty alcohol ether in the first dispersant is from 25 parts by weight to 35 parts by weight and the amount of organic acid ester in the first dispersant is from 40 parts by weight to 50 parts by weight.

Step S120 is a grinding step, grinding the mixture to make a D90 particle diameter of zirconium phosphate range from 0.1 μm to 1.5 μm to form a grinded mixture.

In some embodiments, the D90 particle diameter of zirconium phosphate is from 0.5 μm to 1 μm. If the D90 particle diameter of zirconium phosphate is too large, the mixing uniformity of zirconium phosphate and the first dispersant is poor, and the specific surface area of zirconium phosphate is low, which reduces the deodorization effect of the deodorization fiber formed subsequently. When the D90 particle diameter is larger than 2 μm, the mixture cannot even be spun smoothly in the subsequent melt spinning step. Conversely, when the D90 particle diameter is too small, agglomeration is occur, and the mixing uniformity of zirconium phosphate and the first dispersant is reduced, which decreases the deodorization effect of the deodorization fiber formed subsequently.

In some embodiments, the mixture further includes defoamer (such as silane defoamer) to increase the grinding effect. In some embodiments, an amount of defoamer is from 0.005 parts by weight to 0.02 parts by weight based on an amount of the mixture as 100 parts by weight.

Step S130 is a heating and stirring step, heating and stirring the grinded mixture to uniformly distribute zirconium phosphate and the first dispersant in the solvent to form a deodorant.

It is worth noting that the heat resistance of the first dispersant is poor, and positive groups ($Zr^{4+}$) and negative groups ($PO_4^{3-}$) of zirconium phosphate can represent the charge attraction effect of positive charge and negative charge with the first dispersant, thereby decreasing the degree of thermal damage of the first dispersant (such as the amine group compound, fatty alcohol ether, organic acid ester, or a combination thereof) and maintaining the structure stability of the first dispersant.

In some embodiments, heating and stirring the grinded mixture in the temperature of from 70° C. to 100° C. In some embodiments, the time of the heating and stirring step is from 1 hr to 2 hrs. When the temperature of the heating and stirring step is too high (such as higher than 300° C.) or the time of the heating and stirring step is too long, the possibility of inactivation of the amine group compound by heat is increased. Conversely, if the temperature is too low or the time is too short, the mixing uniformity of zirconium phosphate and the first dispersant is reduced, which decreases the deodorization effect of the deodorization fiber formed subsequently.

Step S140 is a blending and pelletizing step, blending and pelletizing the deodorant and polyester to form a fiber masterbatch.

In some embodiments, at the blending and pelletizing step, the polyester is from 80 parts by weight to 95 parts by weight, and zirconium phosphate is from 5 parts by weight to 20 parts by weight.

In some embodiments, the blending and pelletizing step includes adding the second dispersant to increase lubricity of the deodorant and the polyester. In some embodiments, the second dispersant includes polyester dispersant, paraffin dispersant, or a combination thereof. In some embodiments, the polyester is from 80 parts by weight to 95 parts by weight, zirconium phosphate is from 5 parts by weight to 20 parts by weight, and the second dispersant is from 1 part by weight to 5 parts by weight.

In some embodiments, a temperature of the blending and pelletizing step is from 250° C. to 300° C. If the temperature is too high, the possibility of inactivation of the amine group compound by heat is increased.

Step S150 is a melt spinning step, blending and pelletizing the deodorant and polyester to form a fiber masterbatch.

In some embodiments, the fiber masterbatch is melt spinned in a temperature of from 250° C. to 300° C., If the temperature is too high, the possibility of inactivation of the amine group compound by heat is increased.

It is worth noting that the interference of zirconium phosphate particles to the machine can be decreased by controlling the D90 particle diameter to be lower than 1.5 μm to increase the spinning speed to be, for example, 3000 m/min, and the processing speed can be further increased. If the D90 particle diameter is too large (such as 2 μm), melt spinning cannot even be proceeded smoothly.

The deodorization fiber includes the polyester, zirconium phosphate and the amine group compound, in which D90 particle diameter of zirconium phosphate is from 0.1 μm to 1.5 μm. In some embodiments, the weight ratio of zirconium phosphate and the amine group compound is from 10:1 to 100:1. In some embodiments, the deodorization fiber further includes fatty alcohol ether, organic acid ester, or a combination thereof. In some embodiments, a weight ratio of a total weight of zirconium phosphate and the amine group compound, fatty alcohol ether and organic acid ester is from 1:1 to 10:1.

It is worth emphasizing that zirconium phosphate can convert ammonia gas to ammonium, dissolved in water, and has excellent deodorization effect of ammonia, but has poor deodorization effect of acetic acid. The amine group compound can physically absorb acetic acid by amino group and has excellent deodorization effect of acetic acid, but has poor deodorization effect of ammonia. The deodorization fiber of the present disclosure includes zirconium phosphate and the amine group compound, which has excellent deodorization effect for ammonia and acetic acid, realizing double deodorization. In addition, the deodorization effect of the deodorization fiber will not be reduced even if it is washed by water.

In some other embodiments, after the step S150, the manufacture method 100 includes a staining step, staining the deodorization fiber. It is worth noting that the deodorization effect is not reduced even if the deodorization fiber is stained.

In the following description, multiple embodiments of the present disclosure will be listed to carry out various analysis to verify the efficiency of the present disclosure.

Example 1—Test of Appropriate Particle Diameter of Zirconium Phosphate

First, zirconium phosphate was grinded to obtain zirconium phosphate with different average particle diameters. The deodorization fiber with a specification of 75d/72f was manufactured according to the abovementioned manufacture method. Observe workability of the spinning process, and perform ISO-17299 for testing the deodorization rate of ammonia and acetic acid. In detail, the test of the deodorization rate was performed by manufacturing each group of fiber into a sample to be tested with a size of 10 cm×10 cm, placing the samples to be tested into air bags with ammonia gas with a concentration of 100 ppm or acetic acid gas with a concentration of 100 ppm, respectively, standing for 2 hr, measuring the deodorization rate of each sample to be tested for ammonia gas or acetic acid gas. The result was represented in Table 1.

TABLE 1

| Group | Average Particle Diameter | Workability | Deodorization Rate (Ammonia) | Deodorization Rate (Acetic acid) |
|---|---|---|---|---|
| Comparison (no grinding) | 2 μm | Unable to Spin | X | X |
| Experiment 1 | 1 μm | Poor (Particle Diameter was Too Large) | 51% | 68% |
| Experiment 2 | 550 nm | Good | 84% | 79% |
| Experiment 3 | 300 nm | Poor | 63% | 70% |

6

TABLE 1-continued

| Group | Average Particle Diameter | Workability | Deodorization Rate (Ammonia) | Deodorization Rate (Acetic acid) |
|---|---|---|---|---|
| | | (Powder was Agglomeration) | | |

Note 1:
The deodorization test of Group Comparison could not be conducted since the deodorization fiber could not be manufactured.

Table 1 represented that the deodorization fiber could not be manufactured if the average particle diameter of zirconium phosphate in Group Comparison is 2 μm. Therefore, the melt spinning step could be performed after zirconium phosphate was grinded for reducing the particle size. Average particle diameter of zirconium phosphate in Group Experiment 1 is 1 μm, in which workability was poor since the average particle diameter was too large, and the deodorization effect was not significant since the specific surface area was not enough. Average particle diameter of zirconium phosphate in Group Experiment 3 was 300 nm, in which powder was agglomeration, causing the actual average particle diameter of zirconium phosphate to increase, decreasing workability of spinning, and decreasing the deodorization effect. Average particle diameter of zirconium phosphate in Group Experiment 2 was 550 nm, in which not only workability but also deodorization rate was best.

Example 2—Test of Grinding Condition

For testing which kind of mixture could maintain better stability after grinding, leave the mixtures standstill to observe the changes in appearance and particle diameter after preparing the mixtures of different formulations according to the following Table 2A and carrying out grinding. The result was represented in Table 2B.

TABLE 2A

| Group | Water | Zirconium Phosphate | First Dispersant (Grinding Dispersant) | Defoamer |
|---|---|---|---|---|
| 1 | 58.3% | 35% | 6.7% | Silane Defoamer A (0.01%) |
| 2 | 63.3% | 30% | 6.7% | Silane Defoamer B (0.01%) |
| 3 | 63.3% | 30% | 6.7% | Silane Defoamer A (0.01%) |
| 4 | 55% | 35% | 10% | Silane Defoamer A (0.01%) |
| 5 | 60% | 30% | 10% | Silane Defoamer A (0.01%) |

TABLE 2B

| Group | Z-average (nm) | PDI | D90 (nm) | Stability Test (about 25° C.) |
|---|---|---|---|---|
| 1 | 651.0 | 0.204 | 933 | Gelation after 1 day |
| 2 | 568.9 | 0.197 | 715 | Gelation after 2 days |
| 3 | 544.9 | 0.117 | 745 | Average Particle Diameter was 526.5 nm after 4 Days |
| 4 | 618.6 | 0.248 | 800 | Gelation after 1 day |
| 5 | 654.4 | 0.242 | 876 | Gelation after 1 day |

Note 1:
first dispersant was 30% fatty alcohol ether +45% organic acid ester +10% amine group compound.
Note 2:

TABLE 2B-continued

| Group | Z-average (nm) | PDI | D90 (nm) | Stability Test (about 25° C.) |
|---|---|---|---|---|

Z-average was average particle diameter.
Note 3:
PDI was polydispersity index.

In Table 2B, Group 1-5 had different weight percentages of zirconium phosphate and first dispersant and different kinds of defoamer, zirconium phosphate was grinded to be about from 540 nm to 660 nm through grinding technique. Compared with Group 1 with 35% zirconium phosphate, 6.7% first dispersant and 0.01% silane defoamer A, Group 4 with 35% zirconium phosphate, 10% first dispersant and 0.01% silane defoamer A and Group 5 with 30% zirconium phosphate, 10% first dispersant and 0.01% silane defoamer A, Group 2 with 30% zirconium phosphate, 6.7% first dispersant and 0.01% silane defoamer B and Group 3 with 30% zirconium phosphate, 6.7% first dispersant and 0.01% silane defoamer A had less D90 particle diameter. In stability test, Group 3 represented the best stability, in which Group 3 would not be gelatinized after standing for four days, and the average particle diameter would not be affected. Therefore, Group 3 was selected for the following tests.

Example 3—Test of Structural Protection Effect of Zirconium Phosphate on First Dispersant Under Heating Condition For confirming whether zirconium phosphate protected the first dispersant from structural damage under heating condition, the glass transition temperatures of zirconium phosphate alone, first dispersant alone, and a mixture of zirconium phosphate and first dispersant (zirconium phosphate/first dispersant, weight ratio is 50:1) at different temperatures were compared, in which the average particle diameter of zirconium phosphate was from 400 nm to 800 nm.

Please refer to FIG. 2, the glass transition temperature of the group of zirconium phosphate added alone declined sharply along with the increase of the temperature, which indicated that the structure was damaged by heat. Relatively, the glass transition temperature of the group of zirconium phosphate added alone or the glass transition temperature of the group of zirconium phosphate/first dispersant was not influenced significantly, which indicated the structure were not affected by heat and had good heat stability. That is, the first dispersant was stabilized by zirconium phosphate and the heating damage was decreased.

Example 4—Test of Blending Condition

Group 3 of Example 2 was served as the deodorant. After performing blending and pelletizing according to Table 3A below to form a fiber masterbatch, observe the appearance of the fiber masterbatches, and test ash content, intrinsic viscosity and pressure value of each group. The result was represented in Table 3B.

TABLE 3A

| | | | Second Dispersant Blending Dispersant) | | | |
|---|---|---|---|---|---|---|
| Group | Polyester | Zirconium Phosphate | Polyester Dispersant | Paraffin Dispersant 1 | Paraffin Dispersant 2 | Polyester Dispersant + Paraffin Dispersant 3 + Paraffin Dispersant 4 |
| 1 | 90% | 10% | — | — | — | — |
| 2 | 88% | 10% | 2% | — | — | — |
| 3 | 88% | 10% | — | 2% | — | — |
| 4 | 88% | 10% | — | — | 2% | — |
| 5 | 88% | 10% | — | — | — | 2% |
| 6 | 87% | 10% | — | — | — | 3% |
| 7 | 86% | 10% | — | — | — | 4% |

TABLE 3B

| Group | Ash (%) | Intrinsic Viscosity (IV) | Appearance | Pressure Value (bar/kg) |
|---|---|---|---|---|
| 1 | — | — | White | 50 |
| 2 | 8.67 | 0.662 | White | 2.5 |
| 3 | 8.31 | 0.447 | Yellow | 1.5 |
| 4 | 8.51 | 0.687 | Yellow | 2.5 |
| 5 | 8.96 | 0.671 | Pale Yellow | 2 |
| 6 | 8.84 | 0.781 | Pale Yellow | 1 |
| 7 | 8.23 | 0.676 | Pale Yellow | 2.5 |

Each group of Table 3B had different kinds of second dispersants or the second dispersant with different weight percentages, respectively. In the test of ash, zirconium phosphate of each group was about 8% to 9%. In the test of intrinsic viscosity, the better groups were Group 2 with 2% polyester dispersant, Group 4 with 2% paraffin dispersant 2, Group 5 with 2% second dispersant (polyester dispersant+ paraffin dispersant 3+paraffin dispersant 4), Group 6 with 3% second dispersant (polyester dispersant+paraffin dispersant 3+paraffin dispersant 4) and Group 7 with 4% second dispersant (polyester dispersant+paraffin dispersant 3+paraffin dispersant 4). The groups with better masterbatch appearance were Group 2 and Groups 5 to 7. In the test of pressure value, Group 6 had the lowest pressure value. Based on the above analysis, Group 6 was the best blending and pelletizing condition.

Example 5—Comparison of Influence of Different Ratios of Zirconium Phosphate and First Dispersant on Deodorization Effect According to the abovementioned manufacture method of the deodorization fiber, the deodorization fibers with a specification of 75d/72f were manufactured according to different weight percentages of zirconium phosphate and the first dispersant and processed by different treatments (such as scouring or staining). The test of deodorization rate of ammonia and acetic acid was performed by ISO-17299. The result was presented in Table 4 below, in which the detailed steps of the test of deodorization rate were represented as Example 1, which was not repeated.

TABLE 4

| Group | | Zirconium Phosphate(%) | First Dispersant (%) | Fiber Strength (g/d) | Fiber Elongation (%) | Ammonia Deodorization Rate (%) | Acetic Acid Deodorization Rate (%) | Pocessing |
|---|---|---|---|---|---|---|---|---|
| Comparison | 1 (only polyester) | 0 | 0 | 3.47 | 24.6 | 16 | 50 | Scouring |
| | 2 | 1 | 0 | — | — | 99 | 49 | Finishing |
| | 3 | 1 | 0 | 3.01 | 25.4 | 68 | 49 | Scouring |
| | 4 | 0 | 0.23 | 3.11 | 18.3 | 32 | 78 | Scouring |
| Experiment | 1 | 1 | 0.23 | 3.31 | 24.3 | 82 | 70 | Scouring |
| | 2 | 1.1 | 0.253 | 3.28 | 27.3 | 83 | 71 | Scouring |
| | 3 | 1.2 | 0.276 | 3.20 | 23.3 | 77 | 75 | Scouring |
| | 4 | 1.3 | 0.299 | 3.07 | 29.4 | 77 | 74 | Scouring |
| | 5 | 1.4 | 0.322 | 3.31 | 24.3 | 84 | 79 | Scouring |
| | 6 | 1.5 | 0.345 | 3.04 | 29.8 | 84 | 71 | Scouring |
| | 7 | 1.5 | 0.345 | 3.04 | 29.8 | 87 | — | Scouring + Staining (No Dye Added) |
| | 8 | 1.5 | 0.345 | 3.04 | 29.8 | 94 | — | Scouring + Staining (Dye Added) |
| | 9 | 1.5 | 0.345 | 3.04 | 29.8 | 94 | — | Scouring + Staining (No Dye Added) + Reduction Clearing |

Table 4 represented that Group Experiment 1 to Group Experiment 6 with addition of zirconium phosphate and the first dispersant (the weight percentages of zirconium phosphate and the first dispersant were gradually increased from 1% and 0.23%) were observed that whether the deodorization rate of ammonia or the deodorization rate of acetic acid was significantly increased compared with Comparison group with no addition of zirconium phosphate and the first dispersant. In addition, compared with Group Comparison 2 to Group Comparison 3 with 1% zirconium phosphate, Group Experiment 1 to Group Experiment 6 greatly improved the deodorization rate of acetic acid while maintaining the excellent deodorization rate of ammonia gas. Compared with Group Comparison 4 with 0.23% first dispersant, Group Experiment 1 to Group Experiment 6 greatly improved the deodorization rate of ammonia while maintaining the excellent deodorization rate of acetic acid.

As for Group Experiment) to Group Experiment 6, whether the deodorization rate of ammonia or the deodorization rate of acetic acid was higher than 70%, in which Group Example 5 with 1.4% zirconium phosphate and 0.322% first dispersant represented the best deodorization rate of both ammonia and ammonia.

In addition, Compared with Group 6 with 1.5% zirconium phosphate and 0.345% first dispersant but without staining processing, Group Experiment 7 to Group Experiment 9 with 1.5% zirconium phosphate and 0.345% first dispersant and staining processing were observed that the deodorization rates were not affected even if the deodorization fibers were stained.

Although the disclosure has been disclosed in the above embodiments, it is not intended to limit the disclosure, and it is to be understood that those skilled in the art can make various changes and modifications without departing from the spirit and scope of the disclosure. The scope of protection of the present disclosure is subject to the definition of the scope of claims.

What is claimed is:

1. A manufacture method of a deodorization fiber, including:
a mixing step, mixing zirconium phosphate and a first dispersant including an amine group compound in a solvent to form a mixture;
a grinding step, grinding the mixture to make a D90 particle diameter of the zirconium phosphate range from 0.1 μm to 1.5 μm to form a ground mixture;
a heating and stirring step, heating and stirring the ground mixture to uniformly distribute the zirconium phosphate and the first dispersant in the solvent to form a deodorant;
a blending and pelletizing step, blending and pelletizing the deodorant and polyester to form a fiber masterbatch; and
a melt spinning step, melt spinning the fiber masterbatch to form the deodorization fiber.

2. The manufacture method of the deodorization fiber of claim 1, wherein the mixing step comprises mixing 25 parts by weight to 40 parts by weight of the zirconium phosphate and 5 parts by weight to 15 parts by weight of the first dispersant in 55 parts by weight to 65 parts by weight of the solvent.

3. The manufacture method of the deodorization fiber of claim 1, wherein the first dispersant further comprises fatty alcohol ether, organic acid ester, or a combination thereof.

4. The manufacture method of the deodorization fiber of claim 1, wherein an amount of the amine group compound is from 5 parts by weight to 15 parts by weight based on an amount of the first dispersant as 100 parts by weight.

5. The manufacture method of the deodorization fiber of claim 1, wherein at the blending and pelletizing step, the polyester is from 80 parts by weight to 95 parts by weight, and the zirconium phosphate is from 5 parts by weight to 20 parts by weight.

6. The manufacture method of the deodorization fiber of claim 1, further comprising adding a second dispersant, wherein the second dispersant includes a polyester dispersant, a paraffin dispersant, or a combination thereof at the blending and pelletizing step.

7. The manufacture method of the deodorization fiber of claim 6, wherein at the blending and pelletizing step, the polyester is from 80 parts by weight to 95 parts by weight, the zirconium phosphate is from 5 parts by weight to 20 parts by weight, and the second dispersant is from 1 part by weight to 5 parts by weight.

8. The manufacture method of the deodorization fiber of claim 1, wherein a temperature of the blending and pelletizing step is from 250° C. to 300° C.

9. A deodorization fiber, comprising:

polyester;

zirconium phosphate, wherein a D90 particle diameter of the zirconium phosphate is from 0.1 μm to 1.5 μm; and an amine group compound.

10. The deodorization fiber of claim 9, wherein a weight ratio of the zirconium phosphate and the amine group compound is from 10:1 to 100:1.

\* \* \* \* \*